(12) United States Patent
Gittleman

(10) Patent No.: US 6,309,220 B1
(45) Date of Patent: Oct. 30, 2001

(54) BONE DISTENTION AND CONDENSATION DENTAL IMPLANT DISTRACTOR APPARATUS AND METHOD

(76) Inventor: Neal B. Gittleman, 50 Briar Hollow La., Suite 150 West, Houston, TX (US) 77027

(*) Notice: Subject to any disclaimer, the term of this patent is extended or adjusted under 35 U.S.C. 154(b) by 0 days.

(21) Appl. No.: 09/693,403

(22) Filed: Oct. 20, 2000

(51) Int. Cl.[7] .................................................. A61C 8/00
(52) U.S. Cl. ............................................................. 433/173
(58) Field of Search .................................... 433/173, 172, 433/175; 623/17.15; 606/63, 61

(56) References Cited

U.S. PATENT DOCUMENTS

| | | | | |
|---|---|---|---|---|
| 4,453,539 | * | 6/1984 | Raftopoulos et al. ................. | 128/92 |
| 5,931,674 | * | 8/1999 | Hanosh et al. ...................... | 433/173 |
| 5,976,142 | * | 11/1999 | Chin ..................................... | 606/73 |
| 5,980,522 | * | 11/1999 | Koros et al. ........................... | 606/61 |

* cited by examiner

*Primary Examiner*—John J. Wilson
*Assistant Examiner*—Melba Bumgarner
(74) *Attorney, Agent, or Firm*—Ezra L. Schacht

(57) ABSTRACT

Attempts to install a secure implant post in thinned and receding bone can result in a weakening or loosening of a final restoration and a compromised cosmetic appearance. The current invention remedies the need to drill out a large hole and further thin the receding bone mass by a bone condensing and distension apparatus herein known as an implant distractor. Additionally, the current invention obviates the need for ridge augmentation procedures needed to increase bone mass prior to implant placement. In this invention, a smaller hole is drilled and a vertically sectioned, temporary implant distractor is installed. The implant distractor is split vertically into two or more sectors with cone-shaped concave tapered holes at the coronal and apical ends. A draw screw pulls a cone nut upward into a bottom tapered hole and pulls a typical healing plug with a cone shaped convex lower element into the upper tapered hole to force the implant distractor sectors outward and to expand the surrounding bone. Over time, the vertical sections of this distractor are periodically forced apart to condense and distend the bone to form a wider, stronger bone mass. The distractor is removed and an implant is installed.

13 Claims, 4 Drawing Sheets

BONE DISTENTION AND CONDENSATION DENTAL IMPLANT DISTRACTOR APPARATUS AND METHOD

Through neglect or injury a tooth lost from the anterior maxillary or jaw will result in the loss of supporting bone through resorption. Subsequent attempts to install a secure implant post in the thinned and receded bone can result in a weakening or loosening of the restoration. The current invention remedies the need to drill out a large hole and further thin receding bone mass by a bone condensing and distension apparatus herein known as an implant distractor. Additionally, the current invention obviates the need for ridge augmentation procedures needed to increase bone mass prior to implant placement. In this invention, a smaller hole is drilled and a vertically sectioned, temporary implant distractor is installed. The implant distractor is split vertically into two or more sectors with cone shaped concave tapered depressions at the coronal and apical ends. A draw screw pulls a tapered cone nut upward into the bottom tapered hole and pulls a typical healing plug with a cone shaped convex lower element into the upper tapered hole or depression in the implant distractor. Over time, the vertical sections are forced apart to condense and distend the bone to form a wider, cosmetically desirable bone ridge with increased bone mass surrounding the final implant.

In this manner, the sectors of the implant distractor are spread out to a larger mean diameter to condense the surrounding cancellous bone and distend the alveolar and cortical bone to improve mass and appearance. The size of the initial hole is of lesser diameter than the final distended hole mean diameter. Some vertical cuts or gaps in the alveolar and cortical bone on the anterior labial or buccal side can aid in the repositioning of the alveolar anterior plate to improve appearance and bone mass.

A smaller diameter hole is initially needed to install the implant distractor. Periodic tightening of the draw screw (once every day or so) will force the bone outward. The implant distractor is removed after a suitable time. The final diameter of the hole will be large enough to accommodate a standard implant of commercial manufacture. The surrounding bone having been condensed and outwardly displaced will have the required mass and strength to support the most substantial implant post.

The implant distractor can be equipped with external vertical ribs, projections or grooves on the implant distractor sectors to lock the vertical sectors into the surrounding bone, preventing their rotational movement while the internal draw screw is tightened. Circumferential ribs, projections or grooves can be included to prevent vertical motion during tightening of the implant distractor screw. These ribs engage the inner surface of the bone with enough force to prevent shifting and rotating during the widening process but are backed away from, and no longer engage the bone, during the extraction of the implant distractor.

The implant distractor will have a mirror finish or a non-stick surface to prevent the ingrowth of tissue or bone during the distraction process to facilitate its easy removal after its work is done.

The implant distractor can be constructed in the overall shape of stepped truncated cones or of substantially oval cross sectional profile to better match with CAD/CAM (Computer Aided Design/Computer Aided Machining) manufactured implants. These implant are designed to meet special needs or to better match the emergence profile and root pattern of the original natural tooth.

DETAILED DESCRIPTION OF THE DRAWINGS

Figure 1:
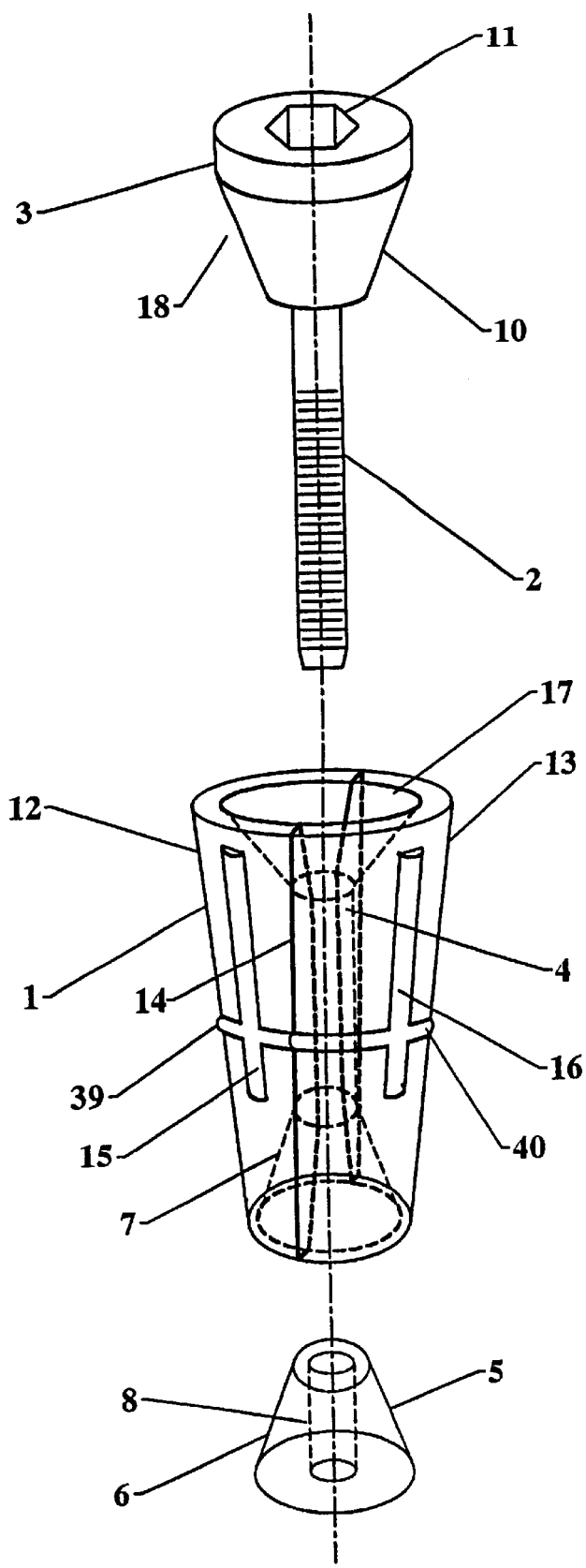
FIG. 1 is an exploded view of a typical split section implant.

FIG. 1 shows a conical dental implant distractor 1 in two vertical sections 12 and 13. These sections have anti-rotational ribs 15 and 16 to prevent the rotation of the implant distractor assembly during tightening. At least one set of circumferential ribs 39 and 40 prevent vertical slippage. Screw 3 with threaded shaft 2 passes through channel 4 and mates with conical nut 5 having an internally threaded hole 8 and an external conical surface 6. Conical surface 6 mates with internal conical surface 7 on the apical end of the implant distractor. Upon tightening the screw into the conical nut, the vertical sections 12 and 13 of the implant distractor are forced apart at the gap 14 and temporarily locked into the surrounding bone by ribs 15, 16, 39 and 40. Cancellous bone is condensed and suitably prepared cortical bone is distracted outwardly to form addition bone mass through new bone growth into the narrow gaps 32 show n in FIGS. 2a, 2b and 3. The conical face 10 on the underside of the screw head mates with internal surface 17 at the coronal end of the implant distractor. Recessed driving means, such as a hex inset 11 is locate on the top surface of the screw 3.

Shaped outer surfaces, other than the conical outer surfaces shown, can be employed to form a hole in the bone and surrounding soft tissue to accommodate commercially available implant posts. It may be preferable to have a stepped cylindrical or stepped conic section outer surface on the implant distractor. A non-circular cross section on the outer surface may more closely mimic the natural tooth root structure and conform the alveolar ridge to a structural and cosmetic advantage. The inner cone shaped surfaces of the underside of the screw head 10 and the cone nut surface 6 need not have circular cross sections as long as surfaces 10 and 17 as well as 6 and 7 slide conformably together. A screw 3 having a separate conical upper element 18 allowed to freely rotate around the screw shaft 2 lets conical element 18 be of a cross section other than round as long as mating surface 10 slides within surface 17 to widen the gap 14. In a similar fashion, the tapered surface 6 of apical nut 5 and mating apical concave depression surface 7 of the implant distractor sectors 13 and 14 can be of a cross section other than round. Apical conical nut 5 can be held captive to the end of draw screw 3 or prevented from disengaging by suitable means to aid in the final removal of all parts of the implant distractor. A flat or other anti-rotation means on matching surface 6 of apical conical nut 5 and a matching flat or other anti-rotation means on surface 7 of implant distractor 1 will prevent nut 5 from spinning freely while the draw screw 3 is being tightened. All elements of the implant distractor can be prepackaged and sterilized as a unit assembly for easy installation. Matching torque tools or wrenches can be used to insure that only enough force is periodically applied to distract the bone without exceeding the mechanical strength limits of the implant distractor elements.

A small wrench with a wide cylindrical head which can be held between the thumb and forefinger and having at the working end a hex projection or socket to engage with the mating drive means located in the top face of screw head 10.

A small conformal, press-on, plastic cap with a rounded external surface can seal the upper surfaces of cap screw and implant distractor for protection against ingress of food particles and to prevent irritation of buccal or lingual tissue surfaces. A small hole or depression in the plastic cap helps in the removal of plastic cap with a dental explorer.

Figure 2A:
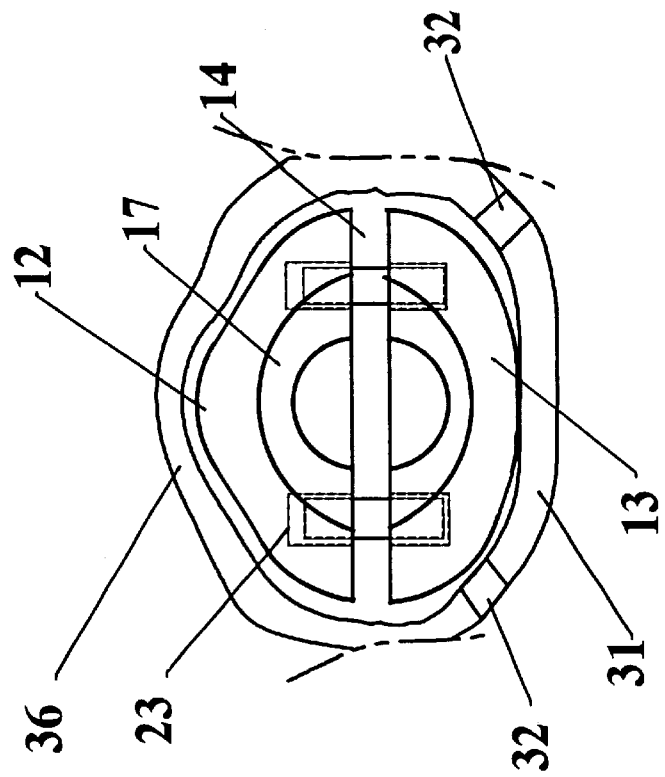
FIG. 2a is a top plan view of a two sector implant distractor.
Figure 2B:
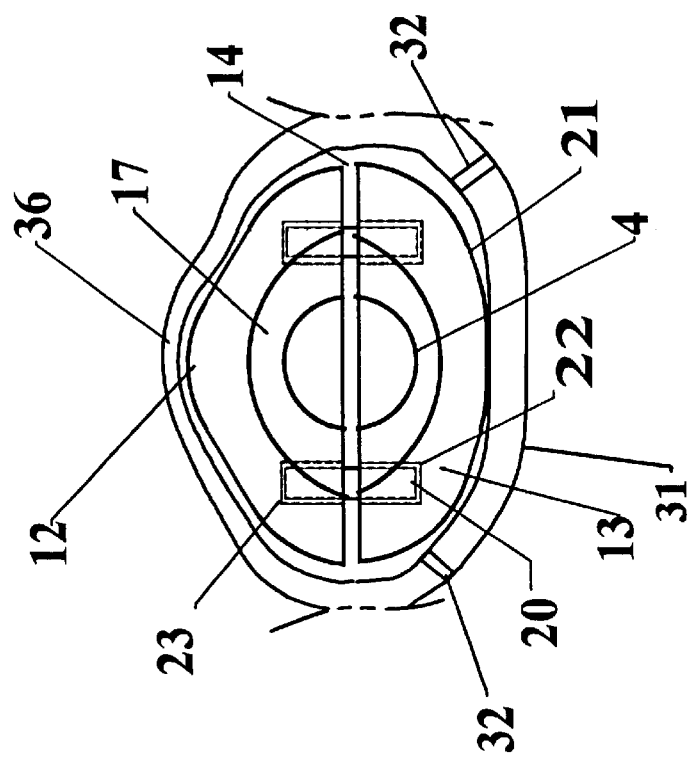
FIG. 2b shows the same implant distractor view with the gap between the sectors widened.

If necessary, means to maintain the sectors of the implant distractor at the same height relative to each other such as mating pins or shaped surfaces at the gap 14 can be employed as detailed in top views FIGS. 2a and 2b. Pins 20 slide conformably within guide holes 22 and 23 to maintain sectors 12 and 13 in vertical alignment.

In the preferred embodiment, surface 10 of draw screw 3 and mating surface 17 need not be true conic sections with circular cross sections. It is only necessary that upon tightening the draw screw, that the surfaces 17 and 10 mate and slide against each other to force vertical sectors 12 and 13 apart. The same conditions apply to surface 6 of the apical nut 5 and surface 7 of the apical end of vertical sectors 12 and 13. Surface 17 is a coronal tapered depression. Surface 7 is an apical tapered depression.

FIG. 2 shows a top view of the implant distractor in closed (a) and opened (b) positions. At least one pin 20 bridges the gap 14 between the two halves of the implant distractor. The pin 20 slides intimately within blind holes 22 and 23 to maintain alignment between the halves of the implant distractor. FIG. 2b shows the assembly in an opened position. The outer profile 21 of the implant distractor is substantially oval in cross section to mimic the natural emergence profile of the tooth being replaced. As the two halves of the implant distractor are forced apart by tightening draw screw 3 (not shown for clarity) the gap 14 widens, forcing the encasing bone to distend outward over time. The bone mass is consolidated and condensed and substantially maintained in strength, mass and thickness by this procedure. The lingual alveolar plate edge 36 can be manipulated by the implant distractor in a similar fashion. Alveolar or cortical bone can be suitably prepared with narrow vertical cuts to facilitate the outward movement of the bone and the growth of new bone within the narrow gaps 32 as the tightening of the implant distractor screw is accomplished over time. Under most circumstances, the alveolar plates may be distracted without the need for cutting vertical gaps 32. A alternative method of site preparation uses a sharp instrument to score at least one vertical groove or gap in the alveolar plate from within the alveolar space. This can be accomplished with several strokes with a scalpel or other hand tool with a small hook shaped sharp cutting edge. By this method, the resection and restoration of gum tissue can be avoided while preparing at least one cantilevered plate of bone.

A preferred method and apparatus for creating vertical cuts in alveolar bone with the proper orientation involves the use of a drilling or cutting template having guides for the introduction of a powered hand tool with a rotating or oscillating cutting bit. The cutting bit is guided by the template to form at least two vertical cuts making at least one cantilevered plate of bone. The cutting tool need not be guided by the template in a direction parallel to the major axis of the implant distractor, but can form a plate with a wider base to preserve the majority of vessels supplying blood to the alveolar bone.

Figure 3:
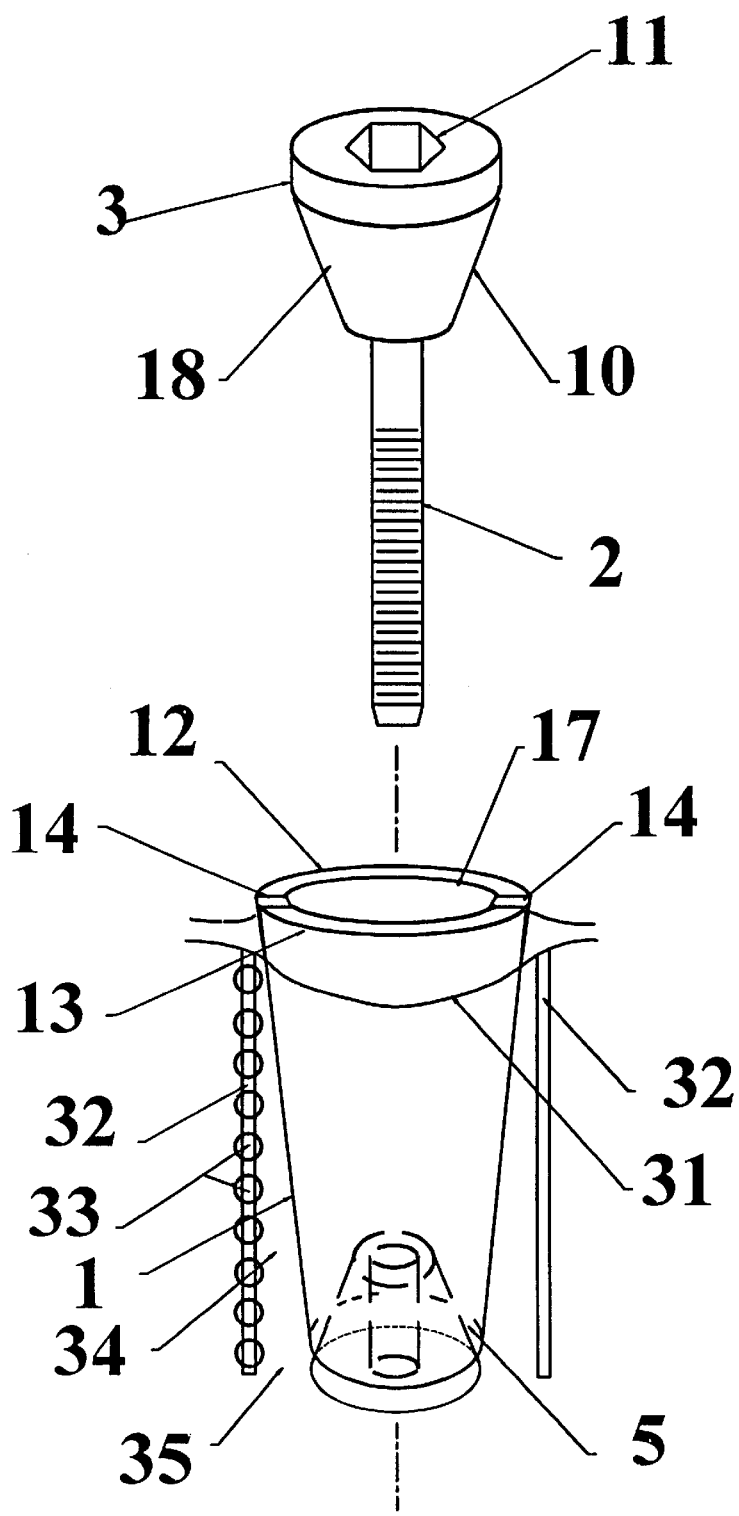
FIG. 3 shows a perspective view of the implant distractor in the installed position within the e alveolar bone.

FIG. 3 shows a typical site preparation with vertical gaps 32 formed from of a series of holes 33. This results in an attached alveolar cantilevered plate of bone 34 The distal edge 31 of the labial alveolar plate 34 is moved outward as the gaps 32 are widened. During the whole procedure, the alveolar plate remains attached to live bone at the flap base 35. The distraction is performed over enough time to result in the growth of new bone within the widening gaps 32 as shown in FIG. 2b and FIG. 3.

Figure 4:
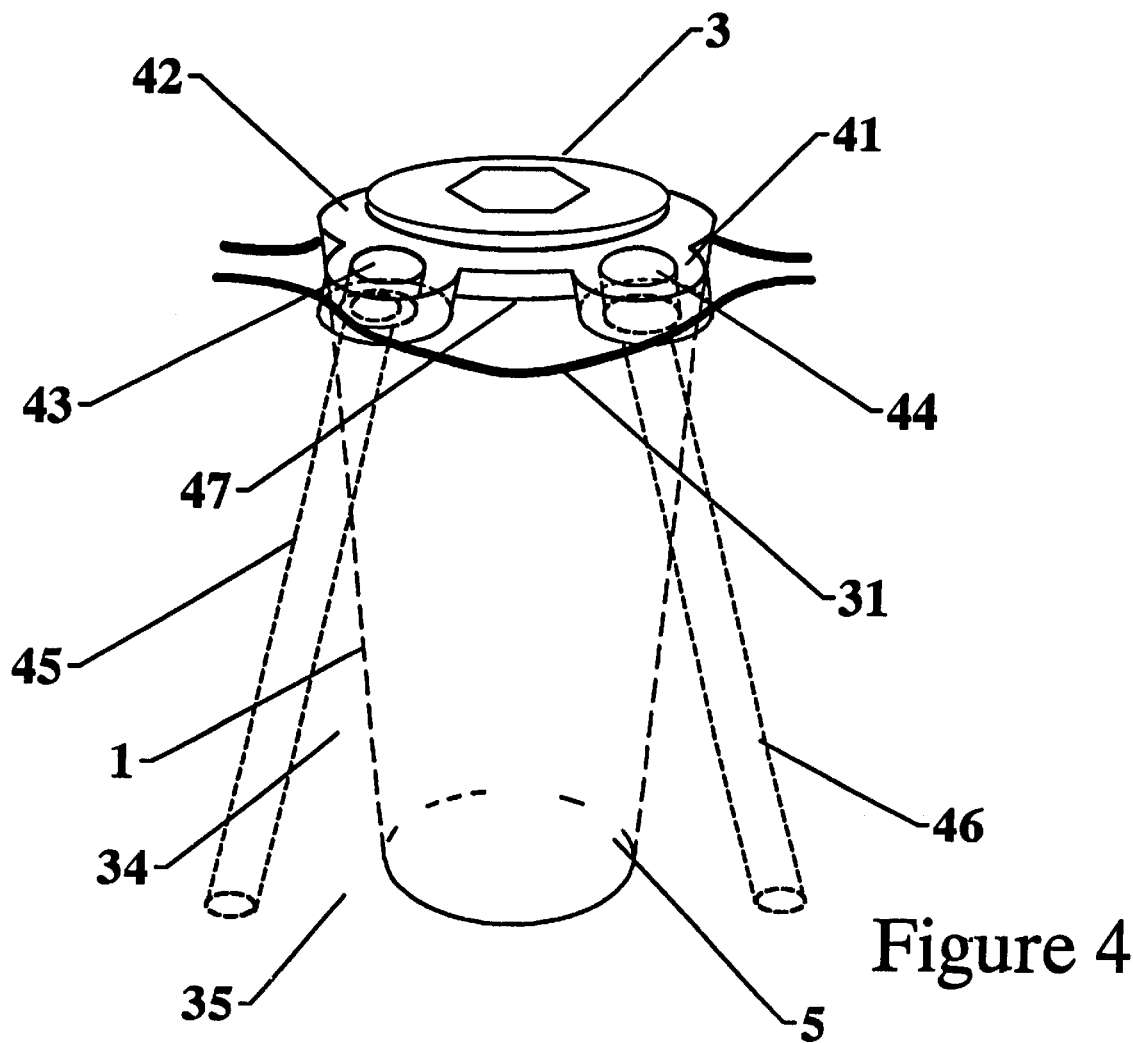
FIG. 4 shows a perspective view of an implant distractor with attached drilling template.

FIG. 4 shows in perspective view, an implant distractor 1 with drilling template 42 fixed to the coronal end of the distractor with draw screw 3 and apical nut 5 (not shown for clarity). The implant distractor with mounting hardware and drill template is pushed into the alveolar space. Drill guide holes 43 and 44 in extended drill guides 41 create by means of a rotating drill or burr one or more channels 45 and 46 in the alveolar and cortical bone. This forms a flap 34 of bone with a distal edge 31 and bone flap base 35. This base 35 is shown wider than the top edge to insure adequate blood supply to the flap during the healing process. An included angle of 15 degrees to the perpendicular is maintained by the drill guide holes 43 and 44 in this representation, but other angles are suitable to the task. By tightening draw screw 3, the drilling template 42 is held in snugly in place while cutting the bone flap. Interface 47 between drilling template 42 and implant distractor 1 has locking means to prevent relative motion between these elements. After the proper gaps 45 and 46 are cut, the draw screw can be unscrewed enough to extract the distractor. The drill guide can then be removed and the distractor reinstalled and tightened in place.

An advantage is offered in using drill guides to precisely form gaps 45 and 46 with the correct width and placement for the easier distension of the flap. New bone grows within these gaps over time with minimal trauma to the overlying soft tissue. The osteogenic tissue bridges the gap while remaining flexible enough to stretch under tension. Strength, mass and rigidity are achieved as this tissue is eventually mineralized.

The template can be included as a separately provided element that is temporarily attached to the top of the implant distractor by means of existing mounting hardware, such as draw screw 3 and apical nut 5. This insures the proper alignment of the template while fixing the implant distractor firmly in the predrilled hole in the bone. Drill guides can be formed as slots to restrict the movement of the drill bit or burr in a single arc-like motion to form narrow gaps from the internal to the external surface of the alveolar bone. The objective is to leave a wide flap base 35 while allowing gaps 45 and 46 to be sufficiently narrow for the proper bridging growth of new cortical bone.

Applicant outlines the steps by which his preferred method is used to apply the implant distractor. First, a small diameter hole is drilled to the necessary depth in the bone. If needed, the alveolar plate is cut into thin vertical gaps 45 and 46 by means of a template guided drill or burr. This prepares one or more vertically cantilevered sections of alveolar bone. Then, the collapsed implant distractor in combination with draw screw 3 and apical conical nut 5 is pressed within the narrow hole. The draw screw 3 is tightened enough to force the implant distractor sectors 12 and 13 outward to condense surrounding cancellous bone and intimately mate with and apply pressure to the surrounding alveolar and cortical bone. A conformal healing cap is placed over the top of the implant distractor. At appropriate intervals, the conformal healing cap is removed and the draw screw is tightened by partial or full turns to force the implant distractor sectors against the surrounding bone to create a larger bore within a thicker bone sheath. When the required bore size has been achieved, the implant distractor is collapsed by loosening draw screw 3 and the sectors 12 and 13, screw 3 and conical apical nut 5 are removed. Next, a commercially or CAD/CAM manufactured implant post is installed with healing hardware and allowed to integrate within the underlying bone. After the appropriate healing time, the healing hardware is removed and a permanent prosthesis is fixed to the implant post.

What is claimed:

1. A dental bone distraction apparatus for widening a bore hole in bone for the installation of a dental implant post comprising:

a dental implant distractor including at least two vertically separated sectors, having in combination a coronal tapered depression and an apical tapered depression;

a draw screw having a threaded shaft and a head including a tapered surface underlying a driven end sliding within the coronal tapered depression of the at least two vertically separated sectors;

an apical tapered nut engaging with said threaded shaft and said tapered nut sliding within said apical tapered depression of said at least two vertically separated sectors;

said draw screw, when tightened into said apical tapered nut, forcing said at least two vertically separated sectors away from each other to effect a wider spacing of said at least two vertically separated sectors for the condensation and distraction of surrounding dental bone.

2. A dental bone distraction apparatus, as described in claim 1, wherein the distractor comprises a smooth exterior surface for easy disengagement from surrounding bone and tissue upon releasing the tension on said draw screw.

3. A dental bone distraction apparatus, as described in claim 1, wherein the distractor comprises a non-cylindrical, exterior surface to mimic the emergence profile of the natural tooth being replaced.

4. A dental bone distraction apparatus, as described in claim 1, wherein the distractor comprises a stepped, truncated conic exterior surface to leave upon extraction, a stepped truncated conic hole in the distracted bone to better match available dental implant posts.

5. A dental bone distraction apparatus, as described in claim 1, wherein the distractor comprises a stepped, cylindrical exterior surface to leave upon extraction a stepped cylindrical hole in the distracted bone to better match available dental implant posts.

6. A dental bone distraction apparatus, as described in claim 1, wherein the distractor comprises a machine profiled exterior surface to leave upon extraction a profiled hole in the distracted bone to better match individually fabricated dental implant posts.

7. A dental bone distractor, as described in claim 1, comprising a locating means between the vertical sectors of said distraction apparatus to maintain said vertical sectors in relative alignment to prevent undue shifting of said vertical sectors during tightening of said draw screw.

8. A dental bone distraction apparatus, as described in claim 1, comprising at least one vertical rib on each vertical sector to prevent rotation while tightening of said draw screw.

9. A dental bone distraction apparatus, as described in claim 1, comprising at least one horizontal rib on each vertical sector to prevent vertical misalignment while tightening said draw screw.

10. A dental bone distraction apparatus, as described in claim 1, comprising a separate drill guide attachable to a coronal end of said dental implant distractor;

said drill guide having at least one hole to direct a dental burr to cut at least one narrow gap in said dental bone.

11. A dental bone distraction method comprising the following steps:

the implant site is prepared by resecting the soft tissue over the underlying bone;

a small diameter hole is drilled in the underlying bone;

a collapsed implant distractor apparatus comprising at least two vertical sectors in combination with a draw screw and apical nut is pressed into said small diameter hole;

said implant distractor apparatus is expanded by means of tightening said draw screw within said apical nut to lock said vertical sectors within said small diameter hole;

the soft tissue is restored and sutured in place leaving said dental bone distraction apparatus with said draw screw accessible;

said draw screw is periodically tightened to condense and distract said dental bone in order to enlarge said vertically drilled hole within thicker surrounding bone;

said dental bone distraction apparatus is removed upon achieving intended hole size by means of loosening said draw screw within said apical nut and collapsing said vertical sectors; and a desired dental implant post is installed in the enlarged hole.

12. A dental bone distraction method, as described in claim 10, in which the underlying bone is prepared for distraction by making at least one surgical cut to improve the distraction of the bone.

13. A dental bone distraction method, as described in claim 10, in which the underlying bone is prepared for distraction by making at least one surgical cut using a drill guide attached to the coronal end of a dental bone implant distractor to improve the distraction of the bone.

* * * * *